US00PP34443P2

(12) United States Plant Patent
Ranney et al.

(10) Patent No.: US PP34,443 P2
(45) Date of Patent: Jul. 26, 2022

(54) ***MAHONIA* PLANT NAMED 'NCMH2'**

(50) Latin Name: *Mahonia*
Varietal Denomination: 'NCMH2'

(71) Applicant: North Carolina State University, Raleigh, NC (US)

(72) Inventors: Thomas Ranney, Arden, NC (US); Darren H. Touchell, Arden, NC (US); Andra Windorf Nus, Mills River, NC (US); Irene Palmer, Mills River, NC (US); Nathan Lynch, Mills River, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/501,735

(22) Filed: Oct. 14, 2021

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Myers Bigel, P.A.

(57) ABSTRACT

'NCMH2' is a new cultivar of *Mahonia* with a compact habit, narrow evergreen foliage, showy red and yellow flowers and red new foliage color.

2 Drawing Sheets

Latin name of the genus and species: The Latin name of the novel, ornamental plant variety disclosed herein is *Mahonia.*

Variety denomination: The inventive cultivar of *Mahonia* disclosed herein has been given the varietal denomination 'NCMH2'.

BACKGROUND OF THE INVENTION

The present invention comprises a new and distinct *Mahonia* cultivar hereinafter referred to by the cultivar name 'NCMH2'. This new *Mahonia*, 'NCMH2', was selected from a population of seedlings grown from an open-pollinated hybrid NCSU H2009-018-063 (unpatented). The first asexual propagation of 'NCMH2' was carried out in December 2014 by rooting stem cuttings in Mills River, N.C. and has been asexually reproduced repeatedly by vegetative cuttings over a 5-year period. 'NCMH2' roots from semi-hardwood and hardwood cuttings were treated with a basal dip of 6,000-10,000 ppm indole butyric acid (potassium salt) in water. 'NCMH2' has been found to retain its distinctive characteristics through successive asexual propagations.

SUMMARY OF THE INVENTION

'NCMH2' is distinguishable from other *Mahonia* cultivars, when grown under standard horticultural practices in Mills River, N.C., by its compact habit; narrow, evergreen foliage; showy racemes with multicolored flowers that bloom sporadically throughout fall, winter, and spring; and showy red new foliage.

BRIEF DESCRIPTION OF THE DRAWINGS

This new *Mahonia* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Mahonia.*

DETAILED BOTANICAL DESCRIPTION

Figure 1:
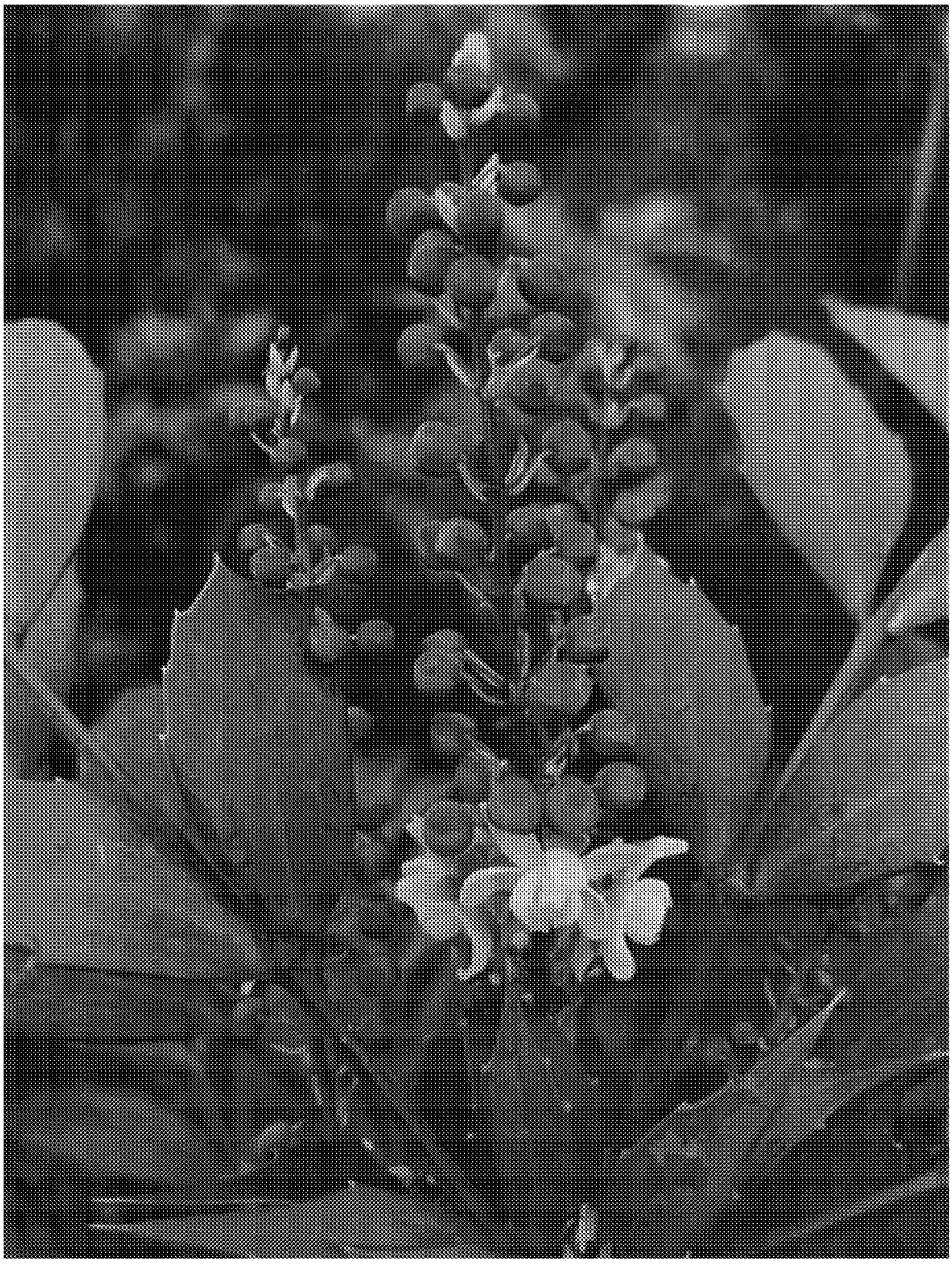
FIG. 1 is a color photograph of a typical specimen of a 3-year-old *Mahonia* 'NCMH2' grown under standard horticultural practices showing the inflorescences of 'NCMH2' taken in October 2019 in Mills River, N.C.
Figure 2:
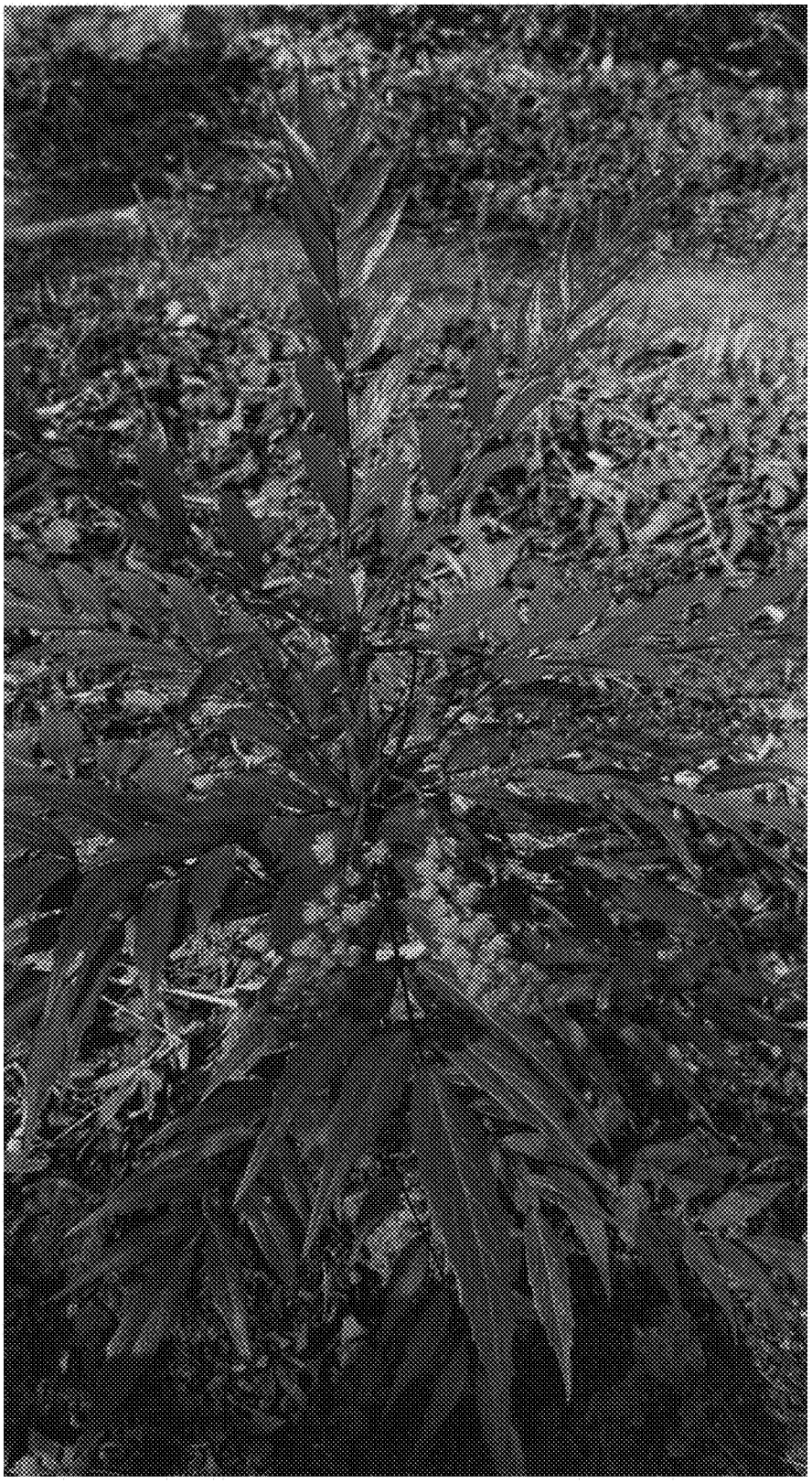
FIG. 2 is a color photograph of a typical specimen of *Mahonia* 'NCMH2' grown under standard horticultural practices showing the flowers, habit, and new foliage color of a two-year old plant of 'NCMH2' growing in Arden, N.C. and taken in March 2019.

Although *Mahonia* species are sometimes classified as *Berberis*, the most recent taxonomic treatment by Yu and Chung *Taxon* 66(6):1371-1392 (2017) classifies *Mahonia* and *Berberis* as separate genera. The following is a detailed description of the botanical characteristics of the new and distinct *Mahonia* variety plant known by the denomination 'NCMH2'. All colors cited herein refer to The Royal Horticultural Society Colour Chart designations (The Royal Horticultural Society (R.H.S.), London, Sixth Edition (2016). Where specific dimensions, sizes, colors, and other characteristics are given, it is to be understood that such characteristics are approximations or averages set forth as accurately as practicable.

The detailed descriptions reported herein were taken in 2019 from a three-year-old container-grown plant that was grown in Mills River, N.C. under standard horticultural practices. *Mahonia* 'NCMH2' has not been observed under all possible environmental conditions; therefore, the phenotype may vary under different environmental conditions such as season, temperature, light intensity, day length, cultural conditions, and the like, without however, any variance in the genotype.

TECHNICAL DESCRIPTION OF THE VARIETY

Classification:

*Botanical name.*—*Mahonia* 'NCMH2'.

*Common name.*—*Mahonia.*

*Variety name.*—'NCMH2'.

Parentage: Selected from a population of seedlings grown from an open-pollinated hybrid, NCSU H2009-018-063 (unpatented). The female parent, H2009-018-063, is a complex hybrid that includes *Mahonia eurybracteata, M. gracilipes, M. japonica*, and *M. lomariifolia* in its pedigree.

Plant description:

*Growth habit.*—Compact and upright shrub.

*Growth rate.*—Moderate.

*Height.*—About 100 cm.

*Width.*—About 60 cm.

Roots:

*Type.*—Fibrous.

*Root color.*—Moderate Yellow (RHS 160A).

Shoot and stem:

*Lateral branch length.*—Average is ~28 cm (~18 cm to ~44 cm).

*Lateral branch diameter.*—Average is ~0.8 cm (~0.5 cm to ~1.2 cm).

*Internode length.*—Average is ~5.4 cm (~3 cm to ~7.5 cm).

*Immature shoot texture* (*current year*).—Glabrous.

*Immature shoot color* (*current year*).—Yellow-Green (RHS 144A).

*Mature stem texture* (*from prior year*).—Glabrous with vertical fissures.

*Mature stem color* (*from prior year*).—Grey-Brown (RHS N199B).

Leaves:

*Type.*—Compound, odd-pinnate.

*Persistence.*—Evergreen.

*Leaf fragrance.*—None.

*Leaf arrangement.*—Alternate.

*Leaf length.*—Average is ~28 cm (~22 cm to ~34 cm).

*Leaf width.*—Average is ~11 cm (~8 cm to ~17 cm).

*Rachis.*—Length: Average is ~17 cm (~12 cm to ~22 cm). Width: About 0.2 cm. Color: Upper side Purple (RHS N77A), lower side Yellow-Green (RHS 144A). Texture: Glabrous.

*Leaflet.*—Arrangement: Opposite with a longer terminal leaflet. Number: 9 to 13 leaflets. Shape: Lanceolate. Apex: Long acuminate. Base: Cuneate. Venation: 3-nerved. Margins: Infrequently serrulate with 6 to 9 teeth. Sub-terminal leaflet length: Average is ~7.3 cm (~5 cm to ~11 cm). Sub-terminal leaflet width: Average is ~1.9 cm (~1 cm to ~2.5 cm). Terminal leaflet length: Average is ~12.3 cm (~10 cm to ~17 cm). Terminal leaflet width: Average is ~2.2 cm (~1.4 cm to ~2.6 cm). Color: Emerging foliage, upper and lower surface: Strong Purplish Red (RHS 64C). Mature foliage, upper surface: Green (RHS 137A). Mature foliage, lower surface: Yellow-Green (RHS 146C). Texture: Glabrous. Attachment: Sessile.

*Leaf attachment.*—Petiolate.

*Petiole.*—Length: Average is ~1.4 cm (~0.7 cm to ~2.6 cm). Diameter: About 0.2 cm. Color: Yellow-Green (RHS 144A), both upper and lower surface. Texture: Glabrous.

Inflorescence:

*Description.*—Single flowers arranged on terminal racemes, opening from base to apex.

*Number of racemes per terminal.*—Average is ~8 (4 to 12).

*Number of flowers per raceme.*—30 to 50.

*Flowering season.*—October to March, sporadically, in Mills River, N.C.

*Fragrance.*—None.

*Lastingness.*—2 to 6 weeks.

*Inflorescence.*—Length: Average is ~12.3 cm (~10 cm to ~14 cm). Width: Average is ~1.8 cm (~1.5 cm to ~2.0 cm).

*Flower.*—Height: Average is ~0.5 cm (~0.5 cm to ~0.6 cm). Diameter: Average is ~1.4 cm (~1.3 cm to ~1.6 cm). Lastingness: 3 to 7 days.

*Bud.*—Shape: Rounded. Diameter, early stage: About 0.2 cm. Diameter, balloon stage: About 0.5 cm. Color, early stage: Vivid Reddish Orange (RHS 42A) with some Vivid Yellow (RHS 17C) and some Strong Reddish Purple (RHS 72B) towards the base. Color, balloon stage: Vivid Reddish Orange (RHS 42A) with increasing amounts of Vivid Yellow (RHS 17C) and some Strong Reddish Purple (RHS 72B) towards the base. Texture: Glabrous.

*Petals.*—Number: 6. Arrangement: Whorled. Length: ~0.5 cm. Width: ~0.3 cm. Shape: Ovate. Margin: Entire. Apex: Rounded. Base: Truncate. Color: Yellow (RHS 8A). Texture: Glabrous.

*Sepals.*—Number: 9, consisting of 6 petaloid sepals and 3 true sepals. Arrangement: Whorled. Petaloid sepals: Length: About 0.8 cm. Width: About 0.3 cm. Shape: Oblong. Margin: Entire. Apex: Obtuse. Base: Rounded. Color, inner surface: Yellow (RHS 8B). Color, outer surface: Yellow (RHS 8B) with some Vivid Reddish Orange (RHS 42A). Texture: Glabrous. True sepals: Length: About 0.5 cm. Width: About 0.3 cm. Shape: Ovoid. Margin: Entire. Apex: Acute. Base: Rounded. Color: Strong Reddish Purple (RHS 72B) at tips and Strong Purplish Red (RHS 63B) at base, both surfaces. Texture: Glabrous.

*Peduncle.*—Length: Average is ~12.4 cm (~6 cm to ~15 cm). Diameter: About 0.1 cm. Color: Greyed-Red (RHS 181C). Texture: Glabrous.

*Pedicels.*—Length: About 0.4 cm. Diameter: Less than 0.1 cm. Color: Greyed-Red (RHS 181C). Texture: Glabrous.

Reproductive organs:

*Gynoecium.*—Pistil number: 1. Pistil length: ~0.4 cm. Stigma shape: Round. Stigma color: Green-Yellow (RHS 1D). Style length: ~0.3 cm. Style color: Green-Yellow (RHS 1D).

*Androecium.*—Stamen number: 6. Stamen shape: Linear. Stamen length: About 0.4 cm. Anther shape: Two-lobed. Anther size: About 0.1 cm. Anther color: Yellow (RHS 7A). Amount of pollen: Moderate. Pollen color: Green-Yellow (RHS 1D).

Fruit and seed:

*Fruit type.*—Berry. Shape: Ovoid. Length: Average is ~0.6 cm (~0.4 cm to ~0.8 cm). Width: Average is ~0.4 cm (~0.3 cm to ~0.7 cm). Color: Greyed-Purple (RHS N186A). Texture: Glabrous, pruinose.

*Seed*.—Number: 1 to 2 per berry. Shape: Ovoid. Length: About 0.5 cm. Width: About 0.3 cm. Color: Yellow-Green (RHS 144C). Texture: Glabrous.

Disease and insect resistance: No significant disease or insect pests have been observed.

Cold hardiness: At least USDA zone 7A; testing has not been completed in colder zones.

COMPARISON WITH PARENTAL SPECIES

'NCMH2' is distinguished from *Mahonia* x *media* 'Winter Sun' in that 'NCMH2' has multicolored flowers of red (RHS 42A) and yellow (RHS 8B), whereas *Mahonia* x *media* 'Winter Sun' has yellow (RHS 7B) flowers. 'NCMH2' is distinguished from *Mahonia* 'Soft Caress' (U.S. Plant Pat. No. 20,183) in that 'NCMH2' has wider evergreen sub-terminal leaflets (about 1.9 cm in width) with reddish (RHS 64C) new growth, whereas *Mahonia* 'Soft Caress' (U.S. Plant Pat. No. 20,183) has narrower evergreen subterminal leaflets (about 0.4 to 0.8 cm in width) and green (RHS 144A) leaflets. 'NCMH2' also has racemes of multicolored flowers, whereas *M*. 'Soft Caress' has yellow (RHS 8A) flowers.

What is claimed is:

1. A new and distinct *Mahonia* plant named 'NCMH2' as illustrated and described herein.

* * * * *